United States Patent [19]

Bowley

[11] 4,111,659

[45] Sep. 5, 1978

[54] MASS AND HEAT TRANSFER EXCHANGE APPARATUS

[75] Inventor: Wallace W. Bowley, Stafford Springs, Conn.

[73] Assignee: Graeme L. Hammond, Hamden, Conn.

[21] Appl. No.: 755,089

[22] Filed: Dec. 27, 1976

Related U.S. Application Data

[63] Continuation-in-part of Ser. No. 509,082, Sep. 25, 1974, abandoned.

[51] Int. Cl.$^2$ ............................................. A61M 1/03
[52] U.S. Cl. ................................ 422/48; 128/DIG. 3; 128/400; 165/170; 210/321 R; 210/321 B
[58] Field of Search ................... 23/258.5 R, 258.5 B, 23/258.5 BH, 258.5 M, 258.5 MH; 128/DIG. 3, 400; 210/321 R, 321 A, 321 B; 165/170

[56] References Cited

U.S. PATENT DOCUMENTS

| | | | |
|---|---|---|---|
| 3,007,680 | 11/1961 | Harris | 165/170 X |
| 3,034,505 | 5/1962 | Sobol | 23/258.5 M |
| 3,060,934 | 10/1962 | Claff et al. | 23/258.5 M |
| 3,140,716 | 7/1964 | Harrison et al. | 128/DIG. 3 UX |
| 3,396,849 | 8/1968 | Lande et al. | 23/258.5 M X |
| 3,480,401 | 11/1969 | Holm et al. | 23/258.5 M |
| 3,489,647 | 1/1970 | Kolobow | 23/258.5 M X |
| 3,502,142 | 3/1970 | McGuffey | 165/170 |
| 3,692,648 | 9/1962 | Matloff et al. | 23/258.5 M UX |
| 3,724,673 | 4/1973 | Ryon | 23/258.5 M X |

*Primary Examiner*—Barry S. Richman
*Attorney, Agent, or Firm*—Paul J. Cook

[57] ABSTRACT

Device suitable for use in heat and mass transfer applications comprising a manifold structure having outwardly extending protrusions from the surface thereof and which is spirally wound into a plurality of convolutions and is surrounded by a shell having a cylindrical body member and conical ends. The protrusions are interconnected with one another so that flow progresses from one to another. The device can be used for heat transfer and for mass transfer between various fluid streams, in particular, venous blood and a stream of oxygen. The manifold structure being spirally wound provides a manifold for oxygen flow in an axial, as well as circumferential, direction. Blood flows axially through the mass transfer device in a plurality of essentially concentric streams. When two manifold structures are provided in tandem in a body member, both heat and mass transfer can be provided with a stream of blood.

9 Claims, 8 Drawing Figures

MASS AND HEAT TRANSFER EXCHANGE APPARATUS

REFERENCE TO RELATED APPLICATION

This application is a Continuation-in-Part of copending application Ser. No. 509,082, filed Sept. 25, 1974 and now abandoned.

BACKGROUND OF THE INVENTION (A) Field of the Invention

This invention relates in general to a device suitable for heat and mass transfer, and, in particular, to a heat and mass transfer device usuable for cooling and oxygenating blood.

(B) Description of the Prior Art

In normal human circulatory systems, the venous blood enters the right heart cavities and is pumped to the lungs. There the blood is oxygenated after which it is returned to the left heart cavities. Arterial blood is then distributed to the body tissues. While passing through the capillary beds of the body, the arterial blood gives-up oxygen, picks-up carbon dioxide, and thus, becomes again the venous blood.

In an artificial cardiorespiratory device, e.g., a total heart-lung bypass, the entire systemic venous blood is prevented from entering the right heart cavities. Instead, it is drained by a mechanical pump into an artificial circuit outside the body and is oxygenated in an artificial gaseous exchange device. The "arterialized" blood is returned by another pump to the systemic arterial system through a cannula in a branch of the aorta. It then perfuses the various capillary beds, but is prevented from entering the blood-heart cavities by the closed aortic valve.

The concept of extracorporeal circulation as an aid to cardiac surgery originated as early as 1937. It was felt that a machine capable of performing the function of the heart and lungs would enable a surgeon to operate upon intra-cardiac abnormalities under direct vision in a relatively dry bloodless field. Meanwhile, the brain, the myocardium, the liver, the kidneys and other tissues would receive adequate flows of oxygenated blood in the artificial heart-lung machine.

The task of replacing adequately the heart and lungs of an average human adult by artificial devices, however, presented a formidable challenge. It took these early investigators more than 15 years of research and development before the gas exchange capacity which permitted extracorporeal circulation in man was achieved. Since about 1950, mechanical oxygenators have evolved from the stage of crude laboratory devices into rather dependable pieces of surgical equipment. There are now three basic classes of artificial lungs being used; the bubble oxygenators, the flm oxygenators, and the membrane oxygenators.

From the wealth of information gained in empirical development and laboratory trials, a concept of the "ideal oxygenator" has immerged. Even now, however, available heart-lung machines still fall short of this idea in many respects.

The qualities of an ideal oxygenator are usually described in terms of the efficient performance of a human lung as the gas exchanger and of the gentleness of the normal circulatory system in handling blood. Most persons skilled in the art agree on the following requirements:

1. The artificial lung must be able to oxygenate up to five liters of venous blood per minute to the range of 95-100 percent saturation.

2. Simultaneously, the gas exchange or mass transfer device must remove carbon dioxide in appropriate amounts so as to avoid either $CO_2$ retention (respiratory acidosis) or $CO_2$ depletion (respiratory alkalosis). A suitably large gas exchange capacity must be provided while keeping the blood content of the artificial lung within reasonable limits.

3. The mechanical process of gas exchange must be gentle enough to avoid destruction of formed elements of the blood or denaturation of plasma proteins.

4. The artificial lung must be of simple design, have as few components as practical and be of dependable construction so as to permit phase oxygenation over prolonged periods, easy cleaning and assembly, and reliable sterilization.

The lungs of an average human adult are able to introduce, according to the metabolic needs of the organisms, from 250 to 5,000 ml. of oxygen into the blood, and to remove about the same amounts of carbon dioxide. This performance requires a gas exchange surface of 80 to 100 $m^2$ and a relatively steady blood volume of 700 to 900 ml. in the lungs, which is continuously removed and replenished at a flow rate varying from 4 to 30 liters per minute.

An artificial lung need only to equal the minimal performance of the human lung, because it is used for perfusion of the resting organism. It should be able, however, to bind up to 300 ml. of oxygen per minute to the venous blood.

Most artificial oxygenators, however, are limited to an oxygen uptake of between 150 and 250 ml./min. Unlike the natural lung, they require an increasingly large surface for gas exchange as the demand for oxygenated blood is augmented. Increased oxygen binding capacity is obtained only at the price of a larger blood volume or content in the oxygenator.

The priming volume of pump oxygenators sufficient in capacity to carry on the perfusion of human adults varies from 1200 to 6000 ml. The largest volumes of blood are almost prohibitive in terms of cost and time required for preparation. On the other hand, there is probably little practical advantage in reducing the priming volume below 1,000 ml. per human perfusion. Most surgeons find it comforting to have a 20 to 60 second supply of blood in the extracorporeal circuit, in case of massive bleeding or any other accident leading to temporary absence of venous return from the organism into the heart-lung machine. Seen in this light, satifying the need for increasingly large priming volumes, as higher flows are required, tends to keep constant the ratio of oxygenator blood content to blood flow. This is a safety factor which cannot be neglected under practical conditions.

During the natural process of blood oxygenation, as occurs in lungs or gills, there is no direct contact between blood and the ambient gas. A semipermeable membrane separates the blood from the oxygen present in the alveolar gas or in the surrounding water. The gas transfer is then evoked by process of molecular diffusion. Since many of the early difficulties encountered in using artificial lungs were associated with froth formation or fibran deposits at the "raw" blood-gas interface, artificial membranes were proposed as a means of protecting the blood from direct exposure to the atmosphere. The concept that respiratory gas transfer is compatible with physical separation of blood and oxygen has evolved into a number of different designs for artificial lungs during the last 10 years or so. In general, howeverever, a membrane oxygenator comprises essentially two membranes between which venous blood is conducted through a gas chamber. Oxygen and carbon dioxide are exchanged across the membranes and arterialized blood is led off.

In membrane oxygenators, a blood film and gaseous oxygen are separated by a semipermeable membrane. Gas transfer across the membrane depends upon the nature of membrane material, its thickness, surface and degree of hydration, and also upon the partial pressure difference of the diffusing gases on opposite sides of the membrane. Theoretical and experimental studies have indicated that $CO_2$ transfer is primarily limited by the membrane barrier, while oxygen transfer is controlled by the thickness of and fluid flow character of the blood film, or in other words by the characteristics of the blood distributing system. Thus, the basic problem in the design of membrane lungs are logistic in nature. Some are associated with the membrane itself, others with the manifolding and distributing system for the blood.

When artificial membranes were first proposed, it was not immediately recognized that carbon dioxide transfer might be more difficult to carry out than oxygen transfer under the particular pressure conditions which prevail in an artificial lung. In the case of an artificial lung, since pure oxygen is used in the gas phase and since the partial pressure of $CO_2$ in blood should not exceed 50 millimeters Hg., a ratio of at least 12:1 exists in favor of oxygen transfer in terms of pressure gradient. Accordingly, to counteract the partial pressure ratio and insure an equal transmission of $CO_2$ and oxygen, the membrane should be 12 times more permeable to $CO_2$ than to oxygen. Only then can a gas exchange ratio of 1 be maintained when the artificial lung is ventilated with pure oxygen.

Unfortunately, most synthetic membranes are only 4 to 5 times more permeable to $CO_2$ than to oxygen, and this is insufficient for the transfer of equal volumes of oxygen and carbon dioxide. Thus, membrane lungs have to be designed in terms of $CO_2$ release, and will therefore feature a considerable reserve in oxygen transfer capacity. In other words, the rate of permeation of $CO_2$ is a bottleneck and dictates the area of the membrane required.

In the liquid and in the gaseous phase on either side of the membrane, $CO_2$ diffuses very rapidly, so that these steps in the gas transfer hardly influence the overall rate of exchange. On the contrary, for the oxygen, factors such as blood film thickness or transit time are critical. It has been established experimentally that the oxygenating capacity of a membrane lung depends much more upon the blood distribution pattern than upon the membrane actually employed. This view is supported by a theoretical analysis of gas diffusion in a membrane lung. When highly permeable membranes are used in a blood oxygenator, the relative permeabilities of the blood film and of the membrane are such that the resistance of the blood film is the controlling factor. As in the case of film oxygenators which do not feature turbulent flow or continuous refilming, the length of the oxygen diffusion path is the rate limiting factor as soon as the thickness of the film exceeds a certain degree as compared to the size of an erythrocyte.

One can thus summarize the logistic problems of the membrane lung by stating that $CO_2$ elimination from the blood depends upon the membrane area available, whereas oxygen uptake into the blood depends upon the design of the blood distributing system.

While logistics is a problem in the design of membrane oxygenators, another common problem associated therewith involves purging of trapped air initially in the blood film flow volume. The necessity for doing this is, of course, obvious as it would be extremely dangerous to allow trapped air to enter the blood stream. Various means have been devised to accomplish the desired purging; however, the primary ones involve tilting, tapping, and shaking of the oxygenator.

Hypothermia as an aid to cardiac surgery developed directly from the work of Bigelow et al. in 1950. Bigelow's fundamental observation was that the oxygen consumption of the warmblooded animal can be reversibly lowered by hypothermia without an oxygen debt being incurred. This reduction in tissue oxygen demand brought about by cooling prompted the idea that low flow perfusion might be usefully associated with hypothermia. The fall in blood temperature observed in most perfusion procedures is no longer feared, but rather is deliberately facilitated by heat-exchange devices. Light (33°-35° C.), moderate (26°-32° C.), and deep (0°-20° C.) hypothermia are commonly used in clinical practice.

In the early stages of clinical heart-lung machine development, temperature regulating devices were incorporated into the extracorporeal circuit to maintain the blood temperature within the normal physiological range. More recently, the success of hypothermic perfusions has led to the development of special heat exchangers of large calorie capacity, which are capable of modifying the temperature of the blood in both directions at a very rapid rate. Heating systems are sometimes required in perfusion equipment because of large metal, glass or plastic parts of heart-lung machines which present tremendous radiating surfaces and are responsible for most of the heat loss from the circulating blood.

Since there is considerable heat loss in all extracorporeal circuits various devices have been introduced for the purpose of maintaining the temperature of the perfused organism within the normal physiological range. Water baths, warm air, infrared radiant energy and heating wires have been used with varying degrees of success. Because of possible thermo injury to the red blood cells, the local temperatures of surfaces in contact with blood should never be permitted to exceed 45° C.

Heretofore, others have disclosed devices comprising membranes having hemispherical protrusions or projections from the membrane for use in blood oxygenation. Such a membrane is shown in U.S. Pat. No. 3,684,097 to Mathewson et al. As disclosed in this patent, two membranes having hemispherical projections therefrom are used in combination, the membranes being disposed so that the projections of one membrane are interdigitated with those of a confronting membrane. This prevents membrane cohesion during storage.

Spiral wound membrane structures are also known, these being shown in U.S. Pat. Nos. 3,489,647 and 3,738,813.

SUMMARY OF THE INVENTION

The present invention, in its basic aspects, is a manifold structure for fluid flow which comprises, in general, an embossed film comprising a base member and extending from a surface thereof a plurality of interconnected spaced-apart projections or protrusions, preferably in the shape of a hemisphere.

The projections are arranged in rows and next adjacent ones in the same row, as well as in adjacent rows, are connected by means of a passageway, preferably having a half cylindrical shape.

A preferred manifold involves two embossed films laminated together in such a fashion that spaced-apart spheres are provided connected together by cylindrical shaped passageways. An inlet is provided for introduction of fluid into a header or manifold from which the fluid flows into a row of spheres. An outlet is provided remote from the inlet of fluid from the manifold structure.

The manifold structure of the invention can be used in either heat or mass transfer exchange applications depending only on which material it is made from. In either instance, however, as a heat or mass transfer device, the manifold will be spirally wound and provided internally of a shell having a cylindrical body member. The body member is provided with such as conical ends, the apex of each of which is provided an opening for an inlet or outlet tube or passageway.

In particular, the invention will find application and provide improved performance as an artificial lung or blood oxygenator wherein it supplants the carbon dioxide in the blood with oxygen.

As a heat and mass transfer device, the invention is distinguished by its simplicity of construction and operation. The manifold of the invention provides large surface area for either mass or heat transfer. It can be constructed of materials that make its overall cost relatively inexpensive, thereby providing a disposable unit.

As a blood oxygenator, the conical ends of the shell around the spirally wound manifold are of critical signification in eliminating entrapped air from the mass transfer device. Moreover, the blood film oxygen transfer is enhanced by encountering multiple spheres as provided in the preferred manifold of the invention.

Quite advantageously, one embodiment of the invention involves the combination of a heat exchanger and blood oxydizer in one device of simple construction. This eliminates the necessity to purchase and operate a separate heat exchanger in conjunction with a blood oxygenator device and attendant with such a product the inconvenience, expense and, of course, the potential danger involved.

BRIEF DESCRIPTION OF THE DRAWING

The invention will be better understood by referring to the drawing in conjunction with reading the specification wherein in.

DETAILED DESCRIPTION OF THE INVENTION AND PREFERRED EMBODIMENTS

Figure 1:
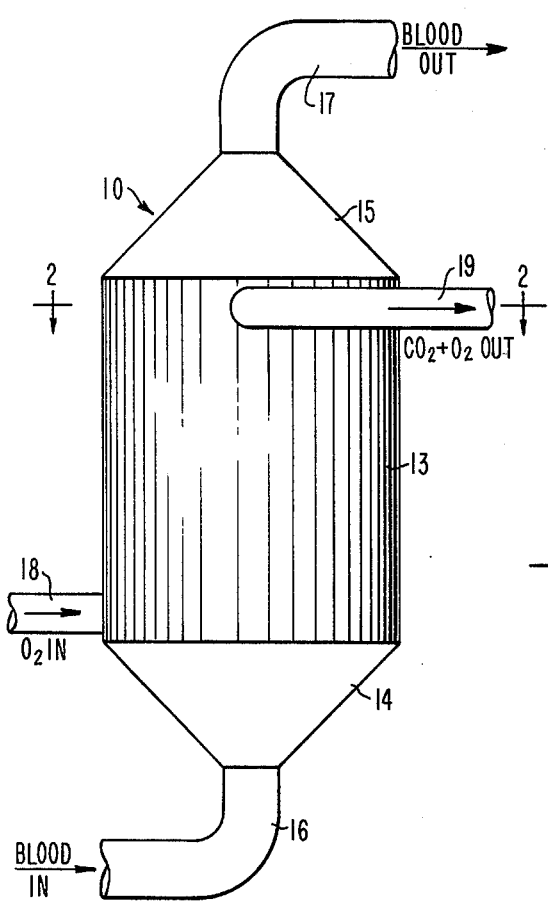
FIG. 1 is shown in elevation a mass transfer device in accordance with the invention.

Turning now to the drawing there is shown in FIG. 1 thereof a mass transfer device 10 according to the invention comprising a shell 11 and a gas manifold 12 comprising a permeable membrane. Shell 11 comprises a cylindrical shaped body member 13 having conical shaped ends 14, 15, one of which at least is removable from the cylindrical body member 13. This permits gas manifold 12 to be inserted in shell 11.

As shown in FIG. 1, an inlet or passageway 16 is provided in conical end 14 for introduction of venous blood into mass transfer device 10, and an outlet or passageway 17 is provided in conical end 15 for passage of arterial blood from the mass transfer device. Each of the passageways, is provided in the apex of the conical ends. As will be appreciated, this provides self purging and precludes any entrapment of air in the blood stream in the mass transfer device which, of course, could be fatal to an individual being operated on. However, it is to be understood that the ends 14 and 15 can be of any geometrical shape so long as provision is made to purge air from the blood in the apparatus of this invention.

Figure 2:
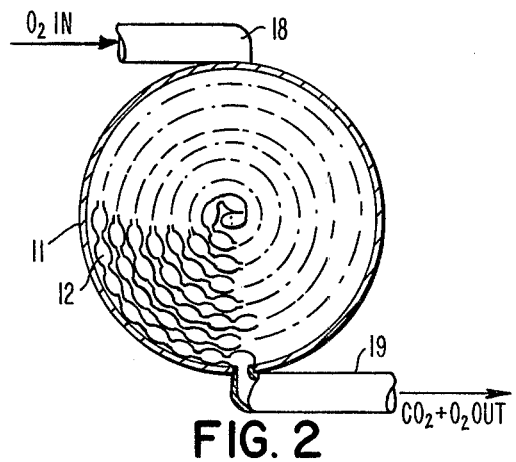
FIG. 2 is shown a cross-section of the device shown in FIG. 1 taken at lines 2—2.
Figure 4:
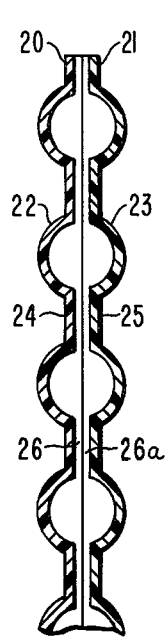
FIG. 4 is a cross-section of the gas manifold shown in FIG. 3 taken at lines 4—4.

Gas permeable membrane 12 is wound in spiral form in a plurality of convolutions, as shown more clearly in FIG. 2, and is provided with an inlet passageway 18 and outlet passagewas 19 integral therewith. The preferred membrane or manifold structure as shown in FIG. 4, comprises two embossed films 20, 21 laminated together in some suitable manner hereinafter described. Each lamina is provided with a plurality of protrusions or projections 22, 23, preferably in the shape of a hemisphere, integral with the respective lamina and extending from the film base 24, 25 on only one side thereof as shown.

The hemispherical shaped projections 22 (FIG. 3) are uniformly spaced from one another over the embossed film and are, arranged, essentially, as seen in the figure, in a plurality of rows. The preferred pattern is a grid work like arrangement of a plurality of horizontal and vertical rows.

Figure 3:
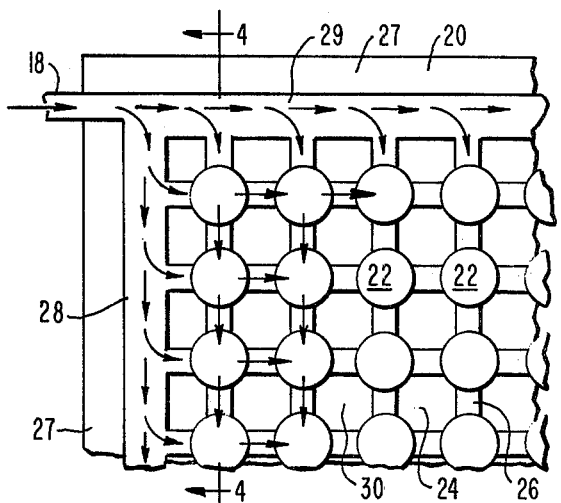
FIG. 3 is a plan view of the manifold structure of the mass transfer device shown in FIG. 1.

As shown in FIG. 3, projections 22 next adjacent one another in each row, whether in vertical or horizontal rows, are connected together by means of passageways 26, 27. These extend from their respective film base on the same side as projections 22, 23. The preferred shape is half cylindrical.

Each embossed film, although not shown explicitly on the drawing, has four corners defining an edge or border 27 (See FIG. 3) of the manifold structure. Inlet 18 is provided as shown at one corner of the manifold structure and is integral with headers or manifolds 28, 29 (similar headers are provided in film 21) which are connected by passageways 26, 26a to each of the respective projections 22, 23 in the rows adjacent thereto.

Although headers 28, 29, which extend outwardly from the film base in the same manner as do pasageways 26, 26a, are preferably half-cylindrical in shape, other configurations can be used. The headers can be, for example, interconnected hemispheres (spheres as shown in FIGS. 3, 4); however, in this case they will be of somewhat larger diameter than projections 22, 23.

Embossed films 20, 21 are laminated together so that projections 22, 23 face in opposite directions as do connecting passageways 26, 26a. As will be seen (FIG. 4), projections 22, 23 and passageways 26, 26a are in mating relationship and out of contact with one another. Thus, in the preferred manifold structure a plurality of spaced apart spheres are interconnected together and to cylindrical shaped headers by means of cylindrical shaped passageways. The embossed films are coextensive and in adhering contact along the edge as well as at locations 30 as shown on film base 24 in between the projections and connecting passageways.

Thus, as will be seen by referring to FIG. 3 of the drawing, a dual manifold arrangement is provided for fluid flow through the gas permeable membrane structure. Flow through the manifold or membrane structure is indicated by the direction of the arrows. A fluid introduced into gas permeable membrane 12 at passageway 18 will divide and flow thereafter in two different directions. This same flow pattern will exist across the manifold as fluid is introduced into each hemispherical projection 22, 23 except, of course, in the case of the projections located at the remote corner of the manifold structure. Fluid flow from each projection converges eventually and exits as a single stream from passageway 19 located at the corner of the laminated membrane structure opposite from that where inlet passageway 18 is located.

In the practice of the invention, the manifold structure is tightly wound in convolutions (FIG. 2) and inserted within shell 13. The tighter the spiral, of course, the thinner the film of blood and the better the oxygenation rate. Winding is most preferably accomplished so that projections 22, 23 interdigate with one another thereby offering a tortuous flow path and enhancing agitation of the blood film as it flows axially along the convolutions of the manifold structure as well as necessitating less priming blood volume.

As will be appreciated, when the blood stream passes upwardly through the spirally wound gas permeable membrane it divides into essentially a plurality of concentric streams of blood, the blood flowing axially through the convolutions formed by the membrane structure. The various streams collect together upon passing the upper edge of the manifold structure and exit as one stream through the exit passageway 17.

The dimensions of the manifold or gas permeable membrane should preferably be as small as practically possible so that the axial distance that the blood flows over a membrane is very small. As is known by those skilled in the art, the shorter the flow distance of the blood, the less chance that there is of damage to the blood components. Thus, the width of embossed film 20 (likewise 21) preferably should be in the range of 5 to 20 cm. The length of the manifold structure when in an unwound state should preferably be at least 500 and up to 2,000 centemeters.

The most desirable manifold structure will have projections 22, (likewise 23) spaced uniformly equidistantly from one another about 2 to 5, preferably 3.5 millimeters center-to-center. Hemispherical projections have a radius of about 1 to 4, preferably 1.25 mm., will offer satisfactory performance in, for example, 5,000 vertical and 36 horizontal rows. With hemispherical projections of such dimensions, the connecting cylindrical passageways should have a radius of about 0.6 mm. It will be appreciated, however that these dimensions are merely exemplary and manifold structures of different dimensions will, of course, be found satisfactory in certain instances.

The dimensions of the shell will, of course, depend upon the particular manifold used, the number of spirals therein, and the desired blood content. With a manifold structure as above described, a satisfactory body member will be an open ended cylinder e.g., 20 centimeters in length, having a diameter of 20 cm. The conical ends will have an apex angle of 120°-150°.

A mass transfer device as above described in which the gas permeable membrane has about 50 turns and is of the size set forth above requires approximately 1200 cc. of blood to prime it.

An oxygenator of the preferred size described above, which occupies a cylindrical space of about 20 × 20 cm., allows an uptake of about 300 cu. cm. of oxygen/the 2.5 sq. meters of surface area/minute, with a comparable exchange of carbon dioxide. The flowrate of the blood through the lung will, of course, be determined by the operator and depend, among other considerations, upon the size of the patient.

In operation, blood is introduced into mass transfer device 10 through inlet 16 and passes axially upward in concentric streams through the convolutions of the gas permeable membrane. It exits therefrom through outlet 17. During passage through the spirally wound membrane, the blood film contacts the protuberances thereby providing for better transfer of oxygen through the membrane and carbon dioxide in the opposite direction. As oxygen passes through the gas manifold (entering at 18), it also diffuses through the membrane entering and thereby oxygenating the blood. At the same time, carbon dioxide diffuses through the membrane from the blood film into the flow spaces between the two embossed lamina and passes from the gas manifold flow membrane via outlet passageway 19, along with the excess oxygen. The blood can be passed through the artificial lung of the invention either by gravity flow or by means of a suitable pump, such as a Sigmamotor or DeBakey pump. Quite advantageously, it will be found, the projections aid in maintaining the blood passageway open. Oxygen pressure on the other hand, keeps the projections and connecting passageways from collapsing.

The manifold structure can be of any material which is gas permeable. Examples of suitable membrane materials include silicone rubber, cellophane, regenerated cellulose, polyethylene, and latex. An ideal material for the embossed film membranes is an organopoly siloxane-polycarbonate block copolymer whose composition is described in U.S. Pat. No. 3,189,622 which is assigned to General Electric Company. A manifold structure made of this material has the high transfer coefficient of carbon dioxide and removes carbon dioxide approximately at the rate of 80% of the rate of oxygen addition which approximates the rate of gas transfer in the human lung. Its transfer coefficient for oxygen is also comparatively high. A membrane made of the above mentioned material also has the desirable property of not tearing catastrophically when it is punctured as do some of the weaker silicone membranes which have been used in blood oxygenators. Other materials can be used, however, a number of these being shown in Table II at page 111 in the book entitled Heart-Lung Bypass published by Grune and Stratton. Typically, the film will have a thickness of from about 0.5 to 2.0 mils.

The shell structure can be of various plastic material, or even of metal. However a clear plastic, which of course should be non-permeable, is most desired. Polyvinyl chloride will be found highly suitable for this purpose.

Embossed films and their lamination to various substrates are of course, well known to those skilled in the molding and laminating art. Thus, it is believed that no detailed explanation will be necessary herein on the manner of manufacturing manifolds in accordance with the invention. This is accomplished, in general, by vacuum molding technique and can be done continuously on vacuum rolls or batch wise in plate molds. In either case, vacuum is applied through mold cavities reflecting the desired size and shape of projection and connecting passageway, as well as header and inlet passageway, to one side of a thermoplastic film while the film is heated to suitable temperature allowing the desired deformation. Two thermoplastic lamina can be passed through the nip formed by two vacuum rolls and embossed simultaneously, if desired, while at the same time heat sealing the lamina together in the desired locations. Heat sealing can be accomplished by means of high frequency radiation or otherwise depending upon the particular thermoplastic gas permeable material used.

In some instances, it may be satisfactory, or even more desirable to use an adhesive rather than heat sealing. The main consideration is that a tight and permanent seal be formed.

Figure 5:
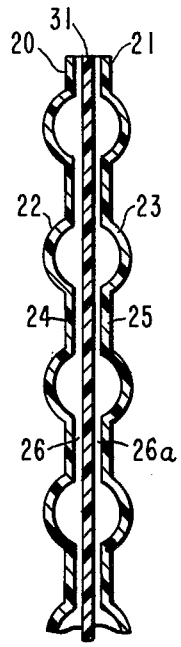
FIG. 5 is an alternative configuration in cross-section of a gas manifold used in conjunction with a mass transfer device according to the invention.

Another but some less efficient embodiment of a gas manifold in accordance with the invention is shown in FIG. 5 of the drawing. Therein intermediate embossed films 20, 21 is provided a flat planar lamina 31.

Figure 6:
FIG. 6 is a view in cross-section of another gas manifold in accordance with the invention.

An even less efficient, but somewhat efficient, gas manifold or permeable membrane is shown in FIG. 6. This embodiment comprises an embossed film 20 having protrusions 22 thereon interconnected by channels or passageway 26 laminated to a planar lamina 31.

Figure 7:
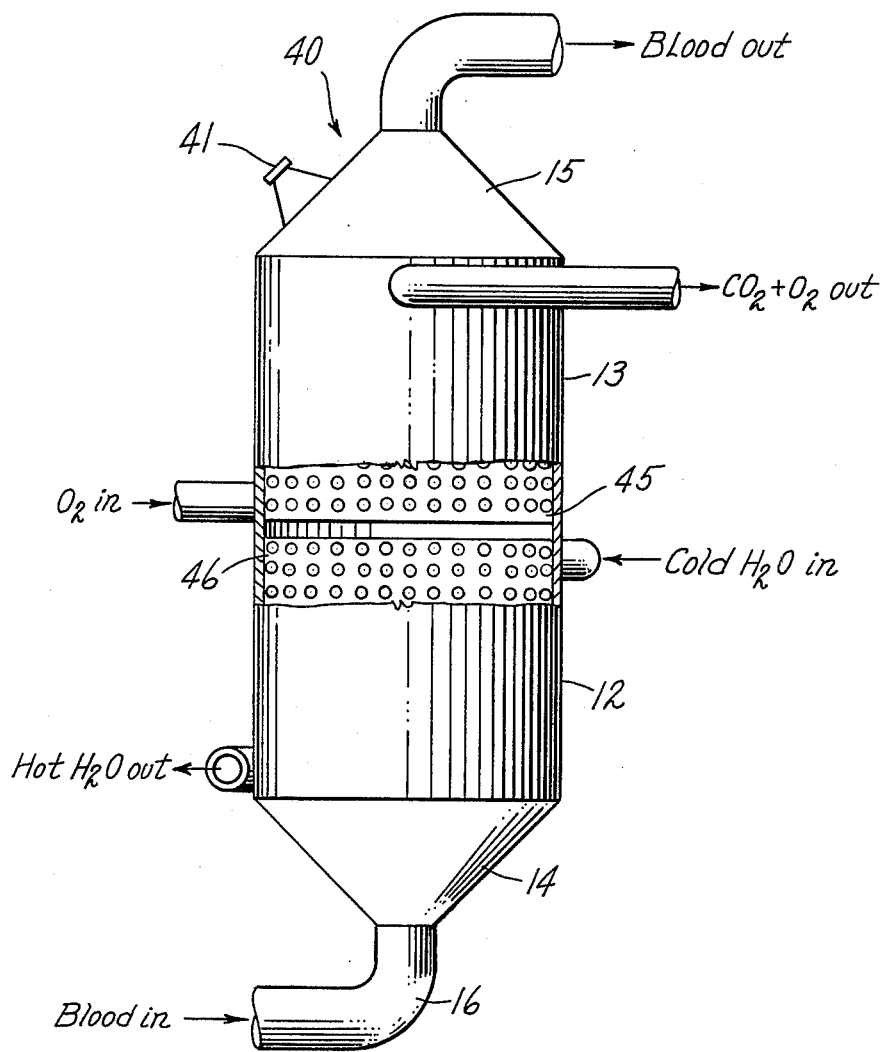
FIG 7 is shown in elevation a device providing both heat and mass transfer in accordance with the invention.
Figure 8:
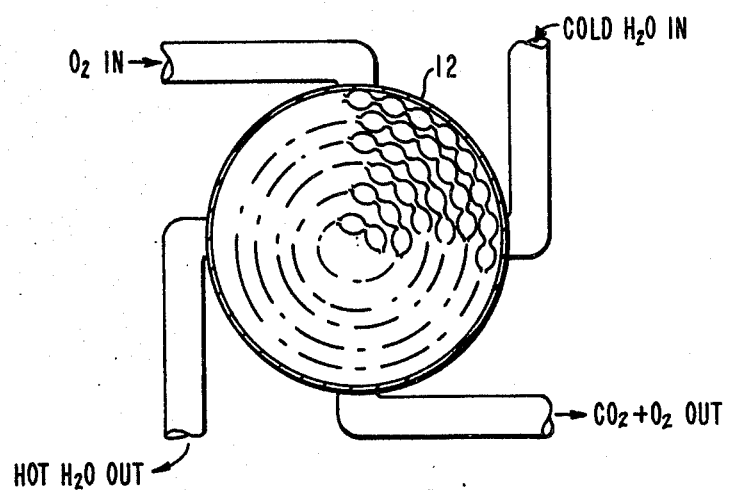
FIG. 8 is a cross-section of the device shown in FIG. 7 taken at lines 8—8.

The manifold structures of this invention can be used not only as mass transfer means but also for heat transfer. Thus, an even more preferred embodiment of the invention is shown in FIGS. 7, 8 of the drawing. Therein (FIG. 7) is shown a device 40 in which two manifold structures 45 and 46, one for heat (46), the other for mass transfer (45), are provided in tandem within a common shell. The blood on entering the shell is cooled (or heated as desired) by a counter current flow of cold water entering the manifold as shown by the arrow. The cooler blood then passes through the oxygenating section where it is then, because it is cool, more readily oxygenated. Sufficient water or other cooling media, and at a suitable temperature, is introduced to maintain the blood at the desired temperature.

Mass transfer can be improved somewhat by flexing the manifold structure during blood passage through the manifold convolutions. This can be accomplished by, for example, an acoustical transducer 41 in operative combination with the shell or body member. Most advantageously, flexing of the manifold structure also results in less protein platelet deposition onto the membrane material.

Although when used as a heat exchanger the manifold structure is of the same general construction as the gas manifold previously described, it is, of course, of a material not permeable to either carbon dioxide or the cooling or heating media. It need not be used in combination with a blood oxygen manifold but can be, if desired, used merely as a heat transfer device. In this case, there may be a single manifold structure in a shell such as shown in FIG. 1 of the drawing. As a heat transfer means it may be found desirable to provide a manifold structure of different dimensions than set forth above. However, the optimum dimensions for any particular application can be readily determined.

The mass transfer device of this invention is equally effective when used as an artificial kidney. However, it will be appreciated that the material of construction of the manifold must be liquid permeable rather than gas permeable. The preferred membrane material for this use is cellophane. Of course, instead of oxygen being passed through membrane 20, 21, a dialyzing fluid is employed instead.

While the mass and heat transfer manifold structures of this invention can be flat, square, rectangular or sinuous in shape, and of varied size in proportion of components, the cylindrical shape illustrated in the drawings is preferred at this time. Equivalent embodiments and materials other than those described above and within the scope and spirit of this invention, will be obvious to those skilled in the art.

I claim:

1. A blood oxygenator comprising a housing having a cylindrically shaped interior and having ends with a blood inlet means and a blood outlet means connected to said ends, a spirally wound membrane means within said housing, said membrane means including an oxygen-containing gas inlet means for said membrane means, a gas outlet means for said membrane means, both said gas inlet and gas outlet means being located external to said housing and a spirally wound membrane structure for mass transfer between an oxygen-containing gas within the first membrane structure and blood within said housing and being formed from at least two membrane sheets wherein at least one of said sheets comprises an embossed semipermeable film having a plurality of spaced-apart projections connected with passageways, said embossed film being permeable to carbon dioxide and oxygen and being sealed to a second membrane to define a fluid path from said membrane inlet means to said outlet means through said projections and passageways.

2. The oxygenator of claim 1 wherein said membrane structure is formed from an embossed film and a planar lamina.

3. The oxygenator of claim 1 wherein said membrane structure is formed from two of said embossed films.

4. The oxygenator of claim 1 wherein said membrane structure is formed from two of said embossed films, each sealed to opposing surfaces of a planar lamina.

5. The oxygenator of claim 1 including means for flexing said membrane structure.

6. A mass and heat transfer apparatus comprising a housing having a cylindrically shaped interior and having ends with a fluid inlet means and a fluid outlet means connected to said ends, a first spirally wound membrane means within said housing, said first membrane means including a first membrane inlet means external said housing, a first membrane outlet means external said housing and a first spirally wound membrane structure for mass transfer between a fluid within the first membrane structure and a fluid within said housing being formed from at least two membrane sheets wherein at least one of said sheets comprises an embossed semipermeable film having a plurality of spaced-apart projections connected with passageways, said embossed film being sealed to another of said membrane sheets to define a fluid path from said first membrane inlet means to said first membrane outlet means and through said projections and passageways, a second membrane means within said housing including a second spirally wound membrane inlet means external said housing, a second membrane outlet means external said housing and a second membrane structure adapted to provide heat transfer between a fluid within the second spirally wound membrane structure and said fluid within the housing, said second membrane structure being in tandem with said first membrane structure and being formed from at least two impermeable sheets wherein at least one of said impermeable membrane sheets comprises an embossed film having a plurality of spaced-apart projections connected with second passageways, said impermeable embossed film being sealed to another of said impermeable membrane sheets to define a fluid path through said second membrane structure from said second membrane inlet means to said second membrane outlet means through said projections and passageways in said second membrane structure.

7. The apparatus of claim 6 wherein said first membrane structure is formed from two of said embossed films.

8. The apparatus of claim 6 wherein said first membrane structure is formed from two of said embossed films each sealed to opposing surfaces of a planar lamina.

9. The apparatus of claim 6 wherein said first membrane structure is formed from an embossed film and a planar lamina.

* * * * *